(12) United States Patent
Truckai et al.

(10) Patent No.: US 8,241,335 B2
(45) Date of Patent: Aug. 14, 2012

(54) BONE TREATMENT SYSTEMS AND METHODS FOR INTRODUCING AN ABRADING STRUCTURE TO ABRADE BONE

(75) Inventors: Csaba Truckai, Saratoga, CA (US); John H. Shadduck, Tiburon, CA (US)

(73) Assignee: DFINE, Inc., San Jose, CA (US)

( * ) Notice: Subject to any disclaimer, the term of this patent is extended or adjusted under 35 U.S.C. 154(b) by 68 days.

(21) Appl. No.: 12/729,004

(22) Filed: Mar. 22, 2010

(65) Prior Publication Data
US 2010/0174286 A1 Jul. 8, 2010

Related U.S. Application Data

(63) Continuation of application No. 11/271,498, filed on Nov. 10, 205, now Pat. No. 7,682,378.

(60) Provisional application No. 60/626,786, filed on Nov. 10, 2004.

(51) Int. Cl.
*A61B 17/88* (2006.01)

(52) U.S. Cl. .......................................... 606/279; 606/79

(58) Field of Classification Search ............... 606/79, 606/80–81, 92–95, 86 R, 279, 90, 105, 180, 606/159
See application file for complete search history.

(56) References Cited

U.S. PATENT DOCUMENTS

| | | |
|---|---|---|
| 3,621,505 A | 11/1971 | Vocker et al. |
| 4,271,839 A | 6/1981 | Fogarty et al. |
| 4,294,251 A | 10/1981 | Greenwald et al. |
| 4,338,925 A | 7/1982 | Miller |
| 4,445,509 A | 5/1984 | Auth |
| 4,827,676 A | 5/1989 | Kindermann |

(Continued)

FOREIGN PATENT DOCUMENTS

EP 1529494 5/2005

(Continued)

OTHER PUBLICATIONS

Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.

*Primary Examiner* — Eduardo C Robert
*Assistant Examiner* — Jan Christopher Merene
(74) *Attorney, Agent, or Firm* — Knobbe Martens Olson & Bear LLP (57) ABSTRACT

The invention provides instruments and methods for prophylactic treatment of an osteoporotic vertebral body or for treating a vertebral compression fracture (VCF). In one exemplary method, a probe system uses a high speed rotational elastomeric cutter having an optional expandable abrasive surface for abrading or cutting at least one path or region within vertebral cancellous bone. Irrigation and aspiration sources are included in the probe system for removing abraded bone debris. In one embodiment, the high speed rotational abrader uses a tissue-selective abrading surface that abrades or cuts bone but does not cut soft tissue. In another embodiment, an expandable abrading surface allows the treatment of bone with low pressures to create paths or spaces without explosive expansion forces known in prior art balloon procedures that are designed to crush and compact cancellous bone in a vertebra. After the creation of a path or space, an in-situ hardenable bone cement volume is introduced into each path or space to support the vertebra.

7 Claims, 12 Drawing Sheets

U.S. PATENT DOCUMENTS

| | | | |
|---|---|---|---|
| 4,857,045 A | 8/1989 | Rydell | |
| 4,895,146 A | 1/1990 | Draenert | |
| 4,969,888 A | 11/1990 | Scholten et al. | |
| 4,969,906 A | 11/1990 | Kronman | |
| 4,990,134 A | 2/1991 | Auth | |
| 5,015,255 A | 5/1991 | Kuslich | |
| 5,059,193 A | 10/1991 | Kuslich | |
| 5,108,404 A | 4/1992 | Scholten | |
| 5,108,405 A * | 4/1992 | Mikhail et al. | 606/96 |
| 5,122,134 A * | 6/1992 | Borzone et al. | 606/80 |
| 5,224,945 A * | 7/1993 | Pannek, Jr. | 606/159 |
| 5,269,785 A | 12/1993 | Bonutti | |
| 5,285,795 A | 2/1994 | Ryan et al. | |
| 5,409,376 A | 4/1995 | Murphy | |
| 5,431,654 A | 7/1995 | Nic | |
| 5,437,655 A | 8/1995 | Bartholomew | |
| 5,499,981 A | 3/1996 | Kordis | |
| 5,514,135 A | 5/1996 | Earle | |
| 5,591,170 A * | 1/1997 | Spievack et al. | 606/82 |
| 5,679,299 A | 10/1997 | Gilbert et al. | |
| 5,693,099 A | 12/1997 | Harle | |
| 5,827,289 A | 10/1998 | Reiley et al. | |
| 5,925,038 A | 7/1999 | Panescu et al. | |
| 5,972,015 A | 10/1999 | Scribner et al. | |
| 6,048,346 A | 4/2000 | Reiley et al. | |
| 6,145,833 A | 11/2000 | Rodewald et al. | |
| 6,171,312 B1 | 1/2001 | Beaty | |
| 6,198,974 B1 | 3/2001 | Webster, Jr. et al. | |
| 6,235,043 B1 | 5/2001 | Reiley et al. | |
| 6,248,110 B1 | 6/2001 | Reiley et al. | |
| 6,261,289 B1 | 7/2001 | Levy | |
| 6,280,456 B1 | 8/2001 | Scribner et al. | |
| 6,284,809 B1 | 9/2001 | Plummer et al. | |
| 6,296,639 B1 | 10/2001 | Truckai et al. | |
| 6,319,255 B1 | 11/2001 | Grundei et al. | |
| 6,332,894 B1 | 12/2001 | Stalcup et al. | |
| 6,358,254 B1 | 3/2002 | Anderson | |
| 6,383,188 B2 | 5/2002 | Kuslich | |
| 6,425,923 B1 | 7/2002 | Stalcup et al. | |
| 6,436,143 B1 | 8/2002 | Ross et al. | |
| 6,439,439 B1 | 8/2002 | Rickard | |
| 6,440,138 B1 | 8/2002 | Reiley et al. | |
| 6,443,967 B1 | 9/2002 | Kadavy et al. | |
| 6,443,988 B2 | 9/2002 | Felt et al. | |
| 6,447,514 B1 | 9/2002 | Stalcup et al. | |
| 6,468,289 B1 | 10/2002 | Bonutti | |
| 6,706,069 B2 | 3/2004 | Berger | |
| 6,712,852 B1 | 3/2004 | Chung et al. | |
| 6,716,216 B1 | 4/2004 | Boucher et al. | |
| 6,719,773 B1 | 4/2004 | Boucher et al. | |
| 6,719,803 B2 | 4/2004 | Bonutti | |
| 6,723,095 B2 | 4/2004 | Hammerslag | |
| 6,726,691 B2 | 4/2004 | Osorio et al. | |
| 6,740,093 B2 | 5/2004 | Hochschuler et al. | |
| 6,746,451 B2 | 6/2004 | Middleton et al. | |
| 6,783,515 B1 | 8/2004 | Miller | |
| 6,783,533 B2 | 8/2004 | Green et al. | |
| 6,790,210 B1 | 9/2004 | Cragg et al. | |
| 6,814,736 B2 | 11/2004 | Reiley et al. | |
| 6,863,672 B2 | 3/2005 | Reiley et al. | |
| 6,923,813 B2 | 8/2005 | Phillips et al. | |
| 6,929,640 B1 | 8/2005 | Underwood | |
| 6,979,352 B2 | 12/2005 | Reynolds | |
| 6,981,981 B2 | 1/2006 | Reiley et al. | |
| 7,008,433 B2 | 3/2006 | Voellmicke et al. | |
| 7,044,954 B2 | 5/2006 | Reiley et al. | |
| 7,143,461 B2 | 12/2006 | Spooner | |
| 7,153,306 B2 | 12/2006 | Ralph | |
| 7,156,861 B2 | 1/2007 | Scribner | |
| 7,166,121 B2 | 1/2007 | Reiley et al. | |
| 7,211,085 B2 | 5/2007 | Michelson | |
| 7,559,932 B2 | 7/2009 | Truckai et al. | |
| 7,641,664 B2 * | 1/2010 | Pagano | 606/92 |
| 7,654,270 B2 | 2/2010 | Gueret | |
| 7,678,116 B2 | 3/2010 | Truckai et al. | |
| 7,682,378 B2 | 3/2010 | Truckai et al. | |
| 7,717,918 B2 | 5/2010 | Truckai et al. | |
| 7,722,620 B2 | 5/2010 | Truckai et al. | |
| 7,901,407 B2 * | 3/2011 | Olson et al. | 606/86 R |
| 2001/0034526 A1 | 10/2001 | Kuslich et al. | |
| 2002/0026195 A1 | 2/2002 | Layne et al. | |
| 2002/0082608 A1 | 6/2002 | Reiley et al. | |
| 2002/0099385 A1 | 7/2002 | Ralph et al. | |
| 2002/0147497 A1 | 10/2002 | Belef et al. | |
| 2002/0183758 A1 | 12/2002 | Middleton et al. | |
| 2002/0188299 A1 | 12/2002 | Reiley et al. | |
| 2003/0032929 A1 | 2/2003 | McGuckin | |
| 2003/0097133 A1 | 5/2003 | Green et al. | |
| 2003/0130664 A1 | 7/2003 | Boucher et al. | |
| 2003/0130738 A1 | 7/2003 | Hovda et al. | |
| 2003/0195547 A1 | 10/2003 | Scribner et al. | |
| 2003/0220648 A1 | 11/2003 | Osorio et al. | |
| 2003/0233096 A1 | 12/2003 | Osorio et al. | |
| 2004/0015218 A1 | 1/2004 | Finch et al. | |
| 2004/0024410 A1 | 2/2004 | Olson | |
| 2004/0073308 A1 | 4/2004 | Kuslich et al. | |
| 2004/0092946 A1 | 5/2004 | Bagga et al. | |
| 2004/0092948 A1 | 5/2004 | Stevens et al. | |
| 2004/0097946 A1 | 5/2004 | Dietzel et al. | |
| 2004/0102845 A1 | 5/2004 | Reynolds | |
| 2004/0110285 A1 | 6/2004 | Lendlein | |
| 2004/0138748 A1 | 7/2004 | Boyer, II et al. | |
| 2004/0147934 A1 | 7/2004 | Kiester | |
| 2004/0167561 A1 | 8/2004 | Boucher et al. | |
| 2004/0186576 A1 | 9/2004 | Biscup et al. | |
| 2004/0193171 A1 | 9/2004 | DiMauro et al. | |
| 2004/0210231 A1 | 10/2004 | Boucher et al. | |
| 2004/0225296 A1 | 11/2004 | Reiss et al. | |
| 2004/0225926 A1 | 11/2004 | Scales | |
| 2004/0228898 A1 | 11/2004 | Ross et al. | |
| 2004/0267271 A9 | 12/2004 | Scribner et al. | |
| 2004/0267272 A1 | 12/2004 | Henniges | |
| 2005/0010231 A1 | 1/2005 | Myers | |
| 2005/0015148 A1 | 1/2005 | Jansen et al. | |
| 2005/0055785 A1 | 3/2005 | Spooner | |
| 2005/0059979 A1 | 3/2005 | Yetkinler | |
| 2005/0180806 A1 | 8/2005 | Green et al. | |
| 2005/0203527 A1 | 9/2005 | Carrison et al. | |
| 2005/0209595 A1 | 9/2005 | Karmon | |
| 2005/0222681 A1 | 10/2005 | Richley et al. | |
| 2005/0245938 A1 | 11/2005 | Kochan | |
| 2005/0251149 A1 | 11/2005 | Wenz | |
| 2006/0052743 A1 | 3/2006 | Reynolds | |
| 2006/0052794 A1 | 3/2006 | McGill et al. | |
| 2006/0074433 A1 | 4/2006 | McGill et al. | |
| 2006/0079834 A1 | 4/2006 | Tennican et al. | |
| 2006/0079905 A1 | 4/2006 | Beyar et al. | |
| 2006/0100635 A1 | 5/2006 | Reiley et al. | |
| 2006/0100706 A1 | 5/2006 | Shadduck et al. | |
| 2006/0122622 A1 | 6/2006 | Truckai et al. | |
| 2006/0122623 A1 | 6/2006 | Truckai et al. | |
| 2006/0149268 A1 | 7/2006 | Truckai et al. | |
| 2007/0198020 A1 | 8/2007 | Reiley et al. | |
| 2008/0114364 A1 * | 5/2008 | Goldin et al. | 606/79 |
| 2008/0208196 A1 | 8/2008 | Daum | |
| 2009/0149878 A1 | 6/2009 | Truckai et al. | |
| 2010/0249785 A1 * | 9/2010 | Betts | 606/79 |

FOREIGN PATENT DOCUMENTS

| | | |
|---|---|---|
| EP | 1787593 | 5/2007 |
| WO | WO 91/06713 | 5/1991 |
| WO | WO 2008/001385 A2 | 1/2008 |

* cited by examiner

BONE TREATMENT SYSTEMS AND METHODS FOR INTRODUCING AN ABRADING STRUCTURE TO ABRADE BONE

CROSS-REFERENCE TO RELATED APPLICATIONS

This application is a continuation of U.S. patent application Ser. No. 11/271,498 filed Nov. 10, 2005, now U.S. Pat. No. 7,682,378, which claims the benefit of Provisional U.S. Patent Application Ser. No. 60/626,786 filed Nov. 10, 2004 titled Systems and Methods for Treating Vertebral Fractures. This application also is related to U.S. application Ser. No. 11/165,652 filed Jun. 24, 2005 titled Bone Treatment Systems and Methods; and U.S. patent application Ser. No. 11/165,651 filed Jun. 24, 2005, titled Bone Treatment Systems and Methods. The entire contents of all of the above cross-referenced applications are hereby incorporated by reference in their entirety and should be considered a part of this specification.

BACKGROUND OF THE INVENTION

1. Field of the Invention

The present invention relates to medical devices, and more particularly to methods and apparatus for treating an abnormal vertebra. More particularly, an apparatus and method includes using a probe carrying a tissue-selective elastomeric rotational cutter having an abrasive surface for abrading or cutting regions within vertebral cancellous bone, with the abrasive surface optionally being expandable in transverse sectional dimension.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the affected population will grow steadily as life expectancy increases. Osteoporosis affects the entire skeleton but most commonly causes fractures in the spine and hip. Spinal or vertebral fractures also have serious consequences, with patients suffering from loss of height, deformity and persistent pain which can significantly impair mobility and quality of life. Fracture pain usually lasts 4 to 6 weeks, with intense pain at the fracture site. Chronic pain often occurs when one level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporotic bone, the sponge-like cancellous bone has pores or voids that increase in dimension, making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. In one percutaneous vertebroplasty technique, bone cement such as PMMA (polymethylmethacrylate) is percutaneously injected into a fractured vertebral body via a trocar and cannula system. The targeted vertebrae are identified under fluoroscopy. A needle is introduced into the vertebral body under fluoroscopic control to allow direct visualization. A transpedicular (through the pedicle of the vertebrae) approach is typically bilateral but can be done unilaterally. The bilateral transpedicular approach is typically used because inadequate PMMA infill is achieved with a unilateral approach.

In a bilateral approach, approximately 1 to 4 ml of PMMA are injected on each side of the vertebra. Since the PMMA needs to be forced into cancellous bone, the technique requires high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using small syringe-like injectors to allow the physician to manually control the injection pressures.

Kyphoplasty is a modification of percutaneous vertebroplasty. Kyphoplasty involves a preliminary step that comprises the percutaneous placement of an inflatable balloon tamp in the vertebral body. Inflation of the balloon creates a cavity in the bone prior to cement injection. Further, the proponents of percutaneous kyphoplasty have suggested that high pressure balloon-tamp inflation can at least partially restore vertebral body height. In kyphoplasty, it has been proposed that PMMA can be injected at lower pressures into the collapsed vertebra since a cavity exists to receive the cement—which is not the case in conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles. Leakage of PMMA during vertebroplasty can result in very serious complications including compression of adjacent structures that necessitate emergency decompressive surgery.

Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (5/2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis. 2003; 62:85-86. The vapors from PMMA preparation and injection are also cause for concern. See Kirby, B., et al., "Acute bronchospasm due to exposure to polymethylmethacrylate vapors during percutaneous vertebroplasty", Am. J. Roentgenol. 2003; 180:543-544.

Another disadvantage of PMMA is its inability to undergo remodeling—and the inability to use the PMMA to deliver osteoinductive agents, growth factors, chemotherapeutic agents and the like. Yet another disadvantage of PMMA is the need to add radiopaque agents which lower its viscosity with unclear consequences on its long-term endurance.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which first crushes and compacts cancellous bone. Expansion of the balloon under high pressures close to cortical bone can fracture the cortical bone, or cause regional damage to the cortical bone that can result in cortical bone necrosis. Such cortical bone damage is highly undesirable and results in weakened cortical endplates.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide systems and methods for use in treatment of vertebral compression fractures that provide a greater degree of control over introduction of bone support material, and that provide better outcomes. Embodiments of the present invention meet one or more of the above needs, or other needs, and provide several other advantages in a novel and non-obvious manner.

SUMMARY OF THE INVENTION

The invention provides systems and methods for treatment of vertebral compression fractures as well as systems and methods for prophylactic treatment of osteoporotic vertebrae in subjects having vertebrae that are susceptible to a compression fracture. The invention also can be used in correcting and supporting bones in other abnormalities such as bone tumors and cysts, avascular necrosis of the femoral head and tibial plateau fractures.

In one embodiment, a probe system is provided that has a working end comprising an elastomeric abrasive cutter that is rotated at high speeds by a motor drive. The rotational elastomeric abrader has a tissue-selective abrading surface that within a selective rpm range can abrade or cut cancellous bone or cortical bone but will not cut soft tissue. The system is used for abrading or cutting at least one path or space within vertebral cancellous bone. Irrigation and aspiration sources are included in the probe system for removing abraded bone debris. After the creation of a path or space in bone, an in-situ hardenable bone cement volume is introduced into each path or space to support the vertebra.

In another embodiment of the invention, a probe system has a working end that comprises an expandable structure having an abrasive surface. In use, the expandable abrading surface is rotated at high speed to cut bone while being expanded to increase the cross section of the path or space being created. The use of the expandable cutter allows the treatment of bone with low pressures to create paths or spaces without explosive expansion forces known in prior art balloon procedures that are designed to crush and compact cancellous bone in a vertebra.

There is a general need to provide systems and methods for use in treatment of vertebral compression fractures that provide a greater degree of control over introduction of bone support material, and that provide better outcomes. The present invention meets this need and provides several other advantages in a novel and nonobvious manner.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

Figure 1:
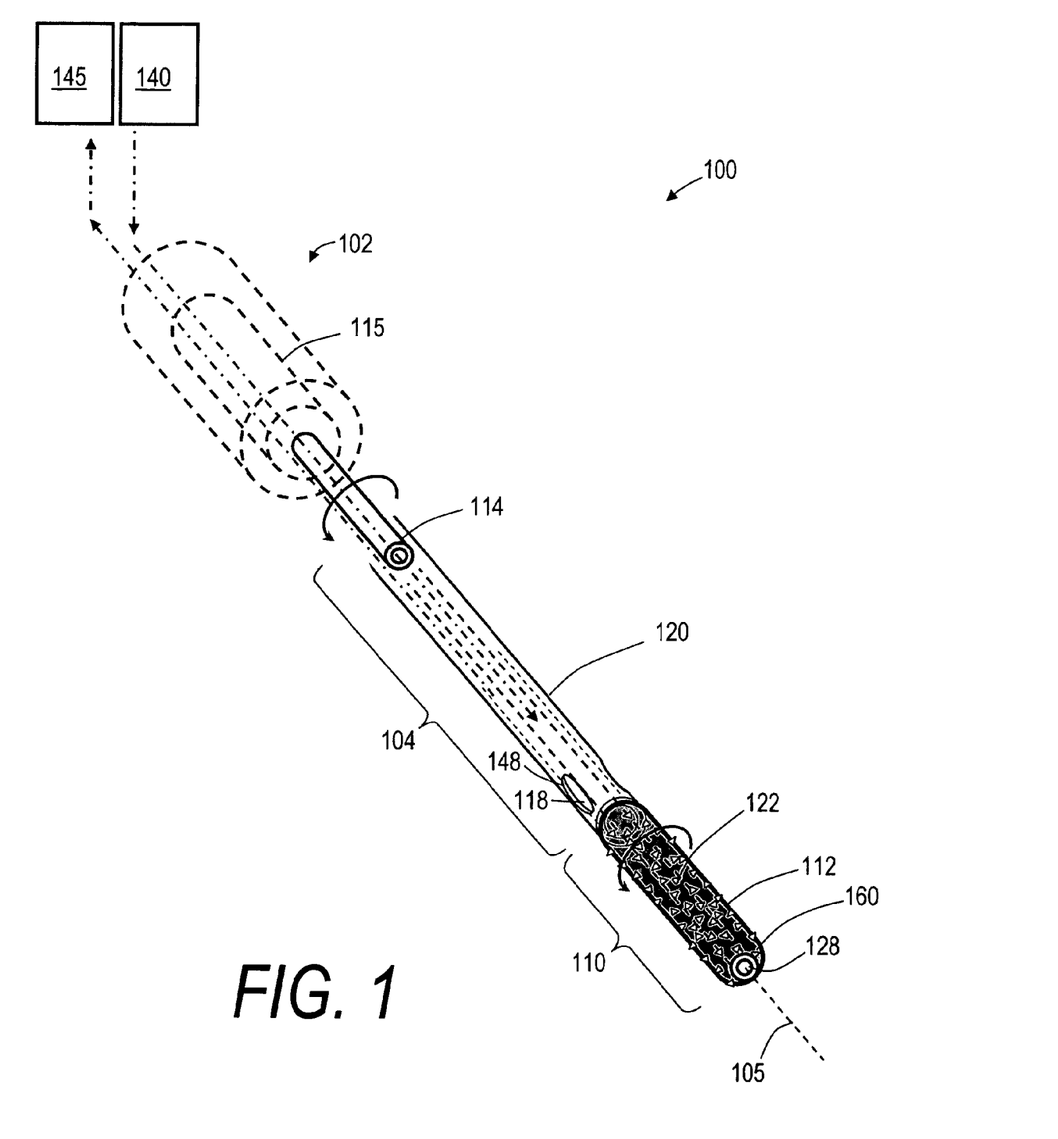
FIG. 1 is a perspective schematic view of an exemplary system of the invention with an elastomeric tissue-discriminating cutter for abrading and cutting bone in an abnormal vertebra.

FIG. 1 is a schematic view of an exemplary bone cutting system or probe 100 that has handle portion 102 that transitions to elongated extension member 104 that extends along axis 105. The extension member 104 carries a distal working end 110 that comprises a high speed elastomeric, abrasive rotational cutter indicated at 112. The handle portion 102 can be any suitable assembly for gripping with a human hand and can carry trigger and actuator mechanisms known in the art.

In the embodiment of FIG. 1, the elastomeric abrasive cutter 112 is fixedly coupled to the distal end of elongated drive member 114 that is rotated at a high speed by a rotation mechanism, such as an air motor or electric motor indicated at 115. The drive member 114 rotates in bore 118 in an elongated rigid sleeve 120 that is coupled to handle portion 102. The elongated sleeve 120 and elastomeric cutter 112 are configured with dimensions suited for insertion into a vertebra from a posterior transpedicular or extrapedicular approach, with the diameter of the sleeve 120 and cutter 112 ranging between about 1.0 mm and 4.0 mm, and more preferably between 1.5 mm and 3.0 mm. The length of the cutter 112 ranges from 1 mm to 10 mm, and more preferably from 2 mm to 5 mm. Of particular interest, the elastomeric cutter 112 is fabricated of a resilient polymer (e.g., silicone or urethane) that is embedded with abrasive crystals 122 or the like, for example diamond or other similar particles having a mean cross-section ranging between about 1 micron and 100 microns, and more preferably between about 5 microns and 50 microns. The rotation mechanism or motor 115 is configured for rotating the elastomeric cutter 112 at speed ranging from about 500 rpm to 400,000 rpm, and more preferably at speeds ranging between about 5,000 rpm and 100,000 rpm.

In the embodiment of FIG. 1, the drive member 114 has a bore 128 therethrough that allows the probe 100 to be advanced over a guide member such as a wire (not shown). The bore 128 also optionally can be used for fluid infusion to irrigate the site, and for this reason a fluid source 140 is shown in FIG. 1. As also shown in FIG. 1, the probe or system 100 optionally includes a negative pressure source 145 operatively connected to bore 118 in sleeve 120 for aspirating fluid and abraded bone debris from the bone treatment site. The distal end portion of sleeve 120 can have ports 148 or openings therein to allow fluid and bone debris to be aspirated into bore 118 of sleeve 120.

The elastomeric cutter 112 can be operated within a selected speed range that preferentially abrades and cuts bone such as cancellous or cortical bone but will not abrade soft tissue. This aspect of the invention is useful, for example, in operations in the interior of a vertebral body, for example when cutting through a cortical wall and inadvertently contacting soft tissue outside the vertebra. The system will discriminate tissue density and not cut the lower density soft tissue such as ligaments. The use of a resilient cutter at selected speeds to discriminate in cutting harder tissue and sparing softer tissue was disclosed in U.S. Pat. Nos. 4,445,509 and 4,990,134 to David C. Auth, which are incorporated herein by this reference. The Auth patents relate to endovascular catheter tips that are abrasive for cutting occlusive materials that clog an artery. The present invention is fabricated in the configuration of a rigid probe 100 with dimensions suited for percutaneous insertion into an abnormal vertebra.

Figure 2A:
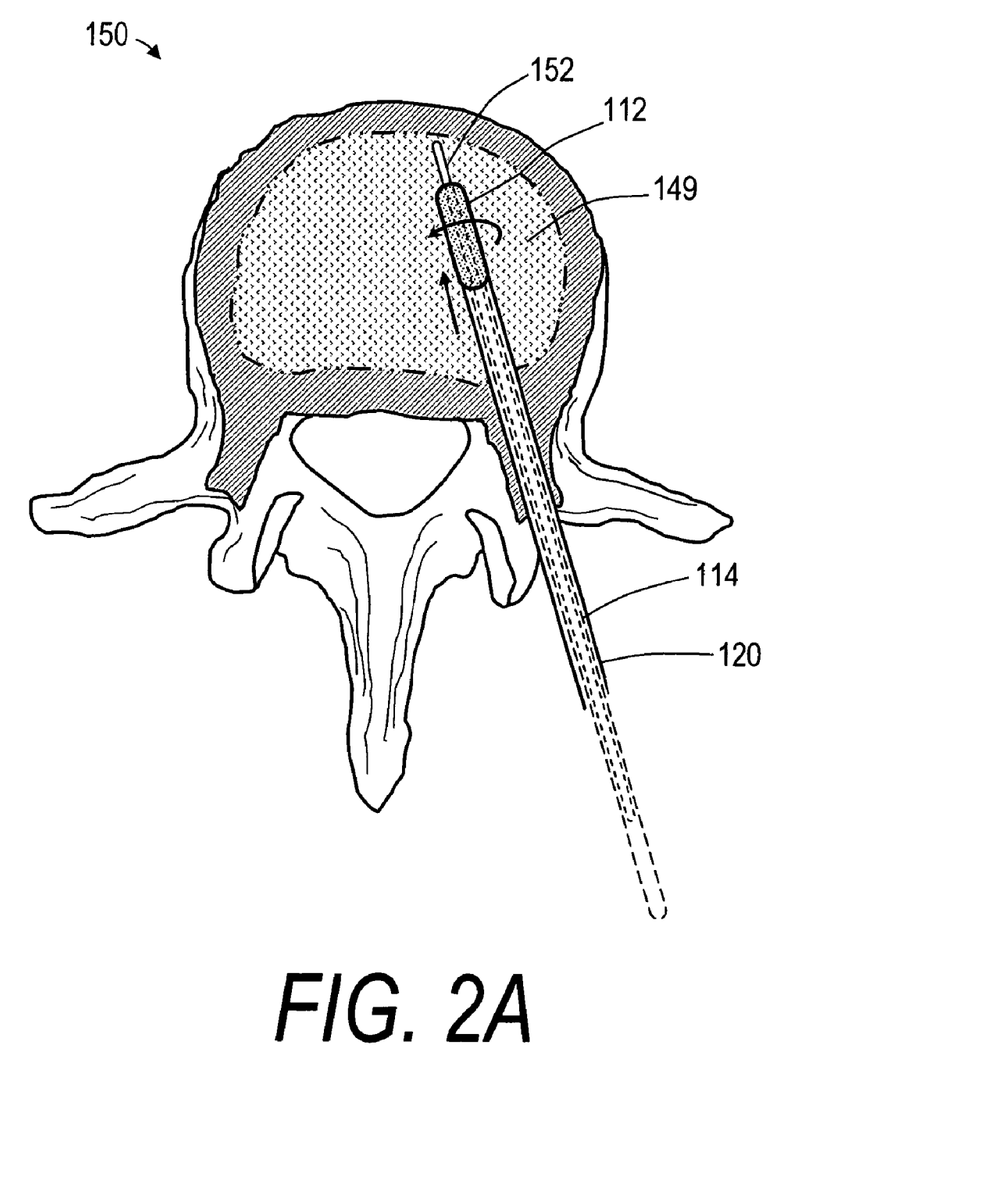
FIG. 2A is a sectional view of a vertebra with an elastomeric cutter similar to that of FIG. 1 being advanced over a straight guide member to abrade a path in cancellous bone.
Figure 2B:
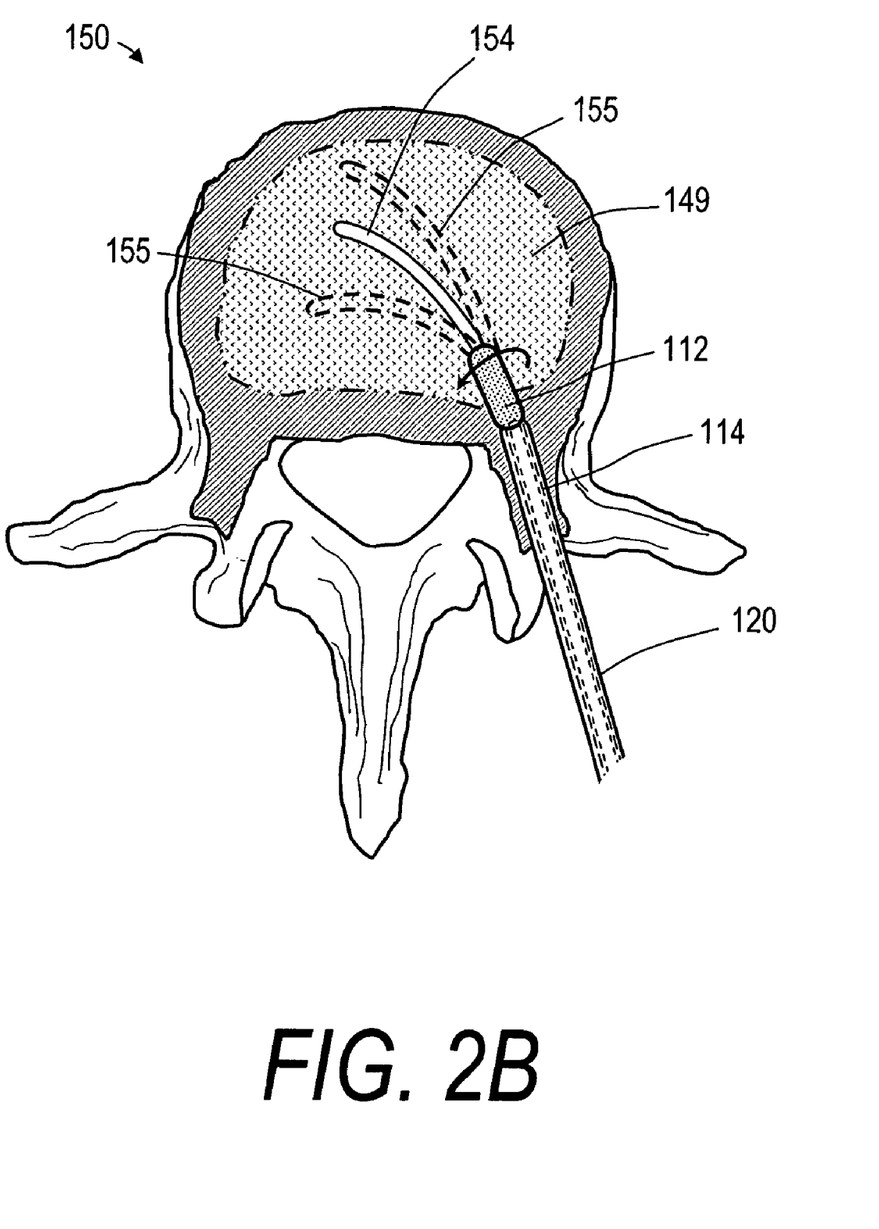
FIG. 2B is a sectional view of an abnormal vertebra with another flexible shaft elastomeric cutter similar to that of FIG. 1 being advanced over at least one curved shape memory guide member to abrade a plurality of paths in cancellous bone.
Figure 3:
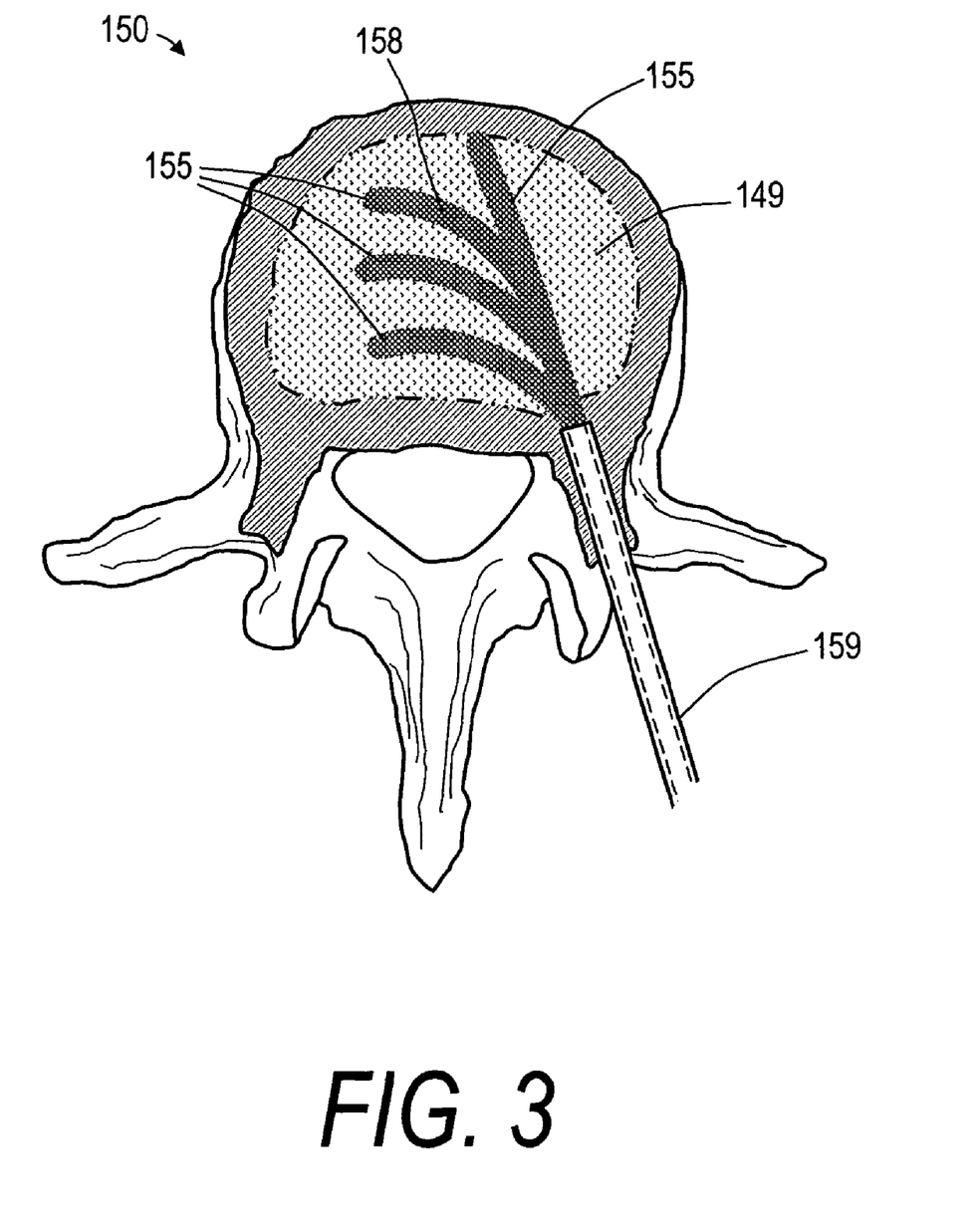
FIG. 3 is a view of the abnormal vertebra of FIG. 2B with the plurality of path in cancellous bone infilled with a hardenable bone cement to reinforce the vertebra.

In one method of use shown in FIGS. 2A and 2B, an elastomeric cutter 112 similar to the embodiment shown in FIG. 1 can be used to cut one or more straight or curved paths in cancellous bone 149 in vertebral body 150. In FIG. 2A, cutter 112 is advanced over a selected straight guide member 152. FIG. 2B illustrates cutter 112 advanced over a curved shape memory alloy guide member 154. In this embodiment, the bore 128 in drive member 114 is dimensioned to slide and rotate relative to the guide member 152 or 154. In the embodiment of FIG. 2B, the drive member 114 can be a helical drive element or braided sleeve that is flexible for rotating the cutter 112. In FIGS. 2A-2B, a plurality of paths 155 can be cut or abraded by this means with the result shown in FIG. 3. In FIG. 3, the plurality of paths 155 are then filled with a bone cement 158 (e.g., PMMA) injected through introducer sleeve 159. The bone cement 158 is adapted to prophylactically treat a vertebra 150 that may be susceptible to a compression fracture.

Figure 4A:
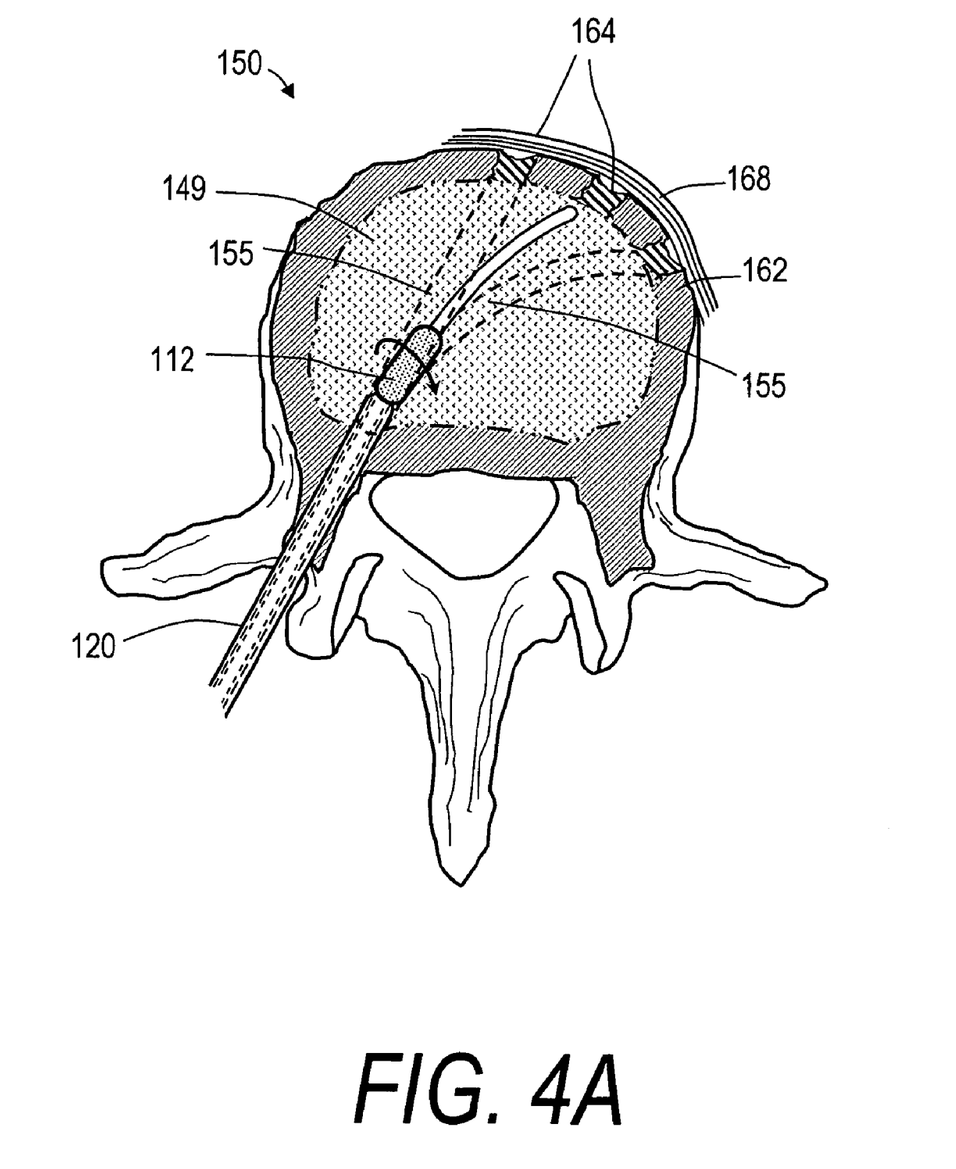
FIG. 4A is a sectional view of another vertebra with a flexible shaft elastomeric cutter similar to that of FIGS. 1 and 2B being used to abrade cortical bone to create a weakened plane.
Figure 4B:
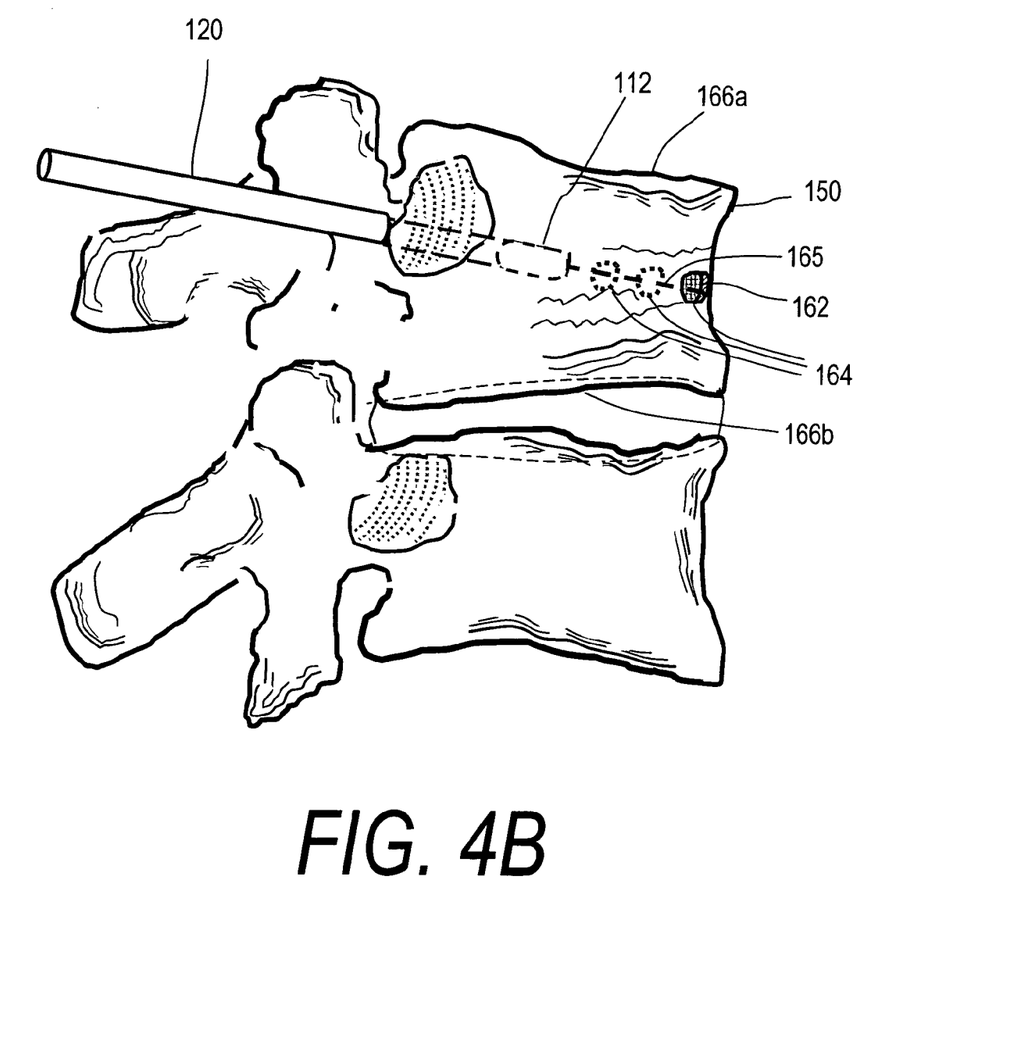
FIG. 4B is a side view of the vertebra of FIG. 4A showing the method of abrading and cutting holes in cortical bone to create a weakened cortical bone region.

In FIGS. 4A-4B, another use of elastomeric cutter 112 is shown wherein tip 160 of the cutter is penetrated through the cortical bone wall 162 of vertebra 150 in at least one location 164 to create a weakened region. This use of the cutter will provide a fracturable region or line 165 in the cortical bone (FIG. 4B) that will allow for elevation of vertebral endplate 166a relative to endplate 166b upon the pressurized introduction of bone fill materials. This use of cutter 112 as indicated in FIGS. 4A-4B is adapted for cases in which a vertebral compression fracture has healed in a collapsed position with the bone portions fusing together. The cutter 112 thus allows cutting through cortical bone 162 with the cutter abrading bone but discriminating tissue based on density differences so that the cutter does not cut the ligaments 168 as the cutter tip 160 penetrates cortical bone layer 162. (FIG. 4A). This method of creating a weakened plane or region 165 in cortical bone was disclosed by the authors in U.S. Provisional Patent Application Ser. No. 60/622,209 filed Oct. 26, 2004 titled Systems and Methods for Treating Vertebral Fractures, which is incorporated herein by this reference and made a part of this specification.

Figure 5:
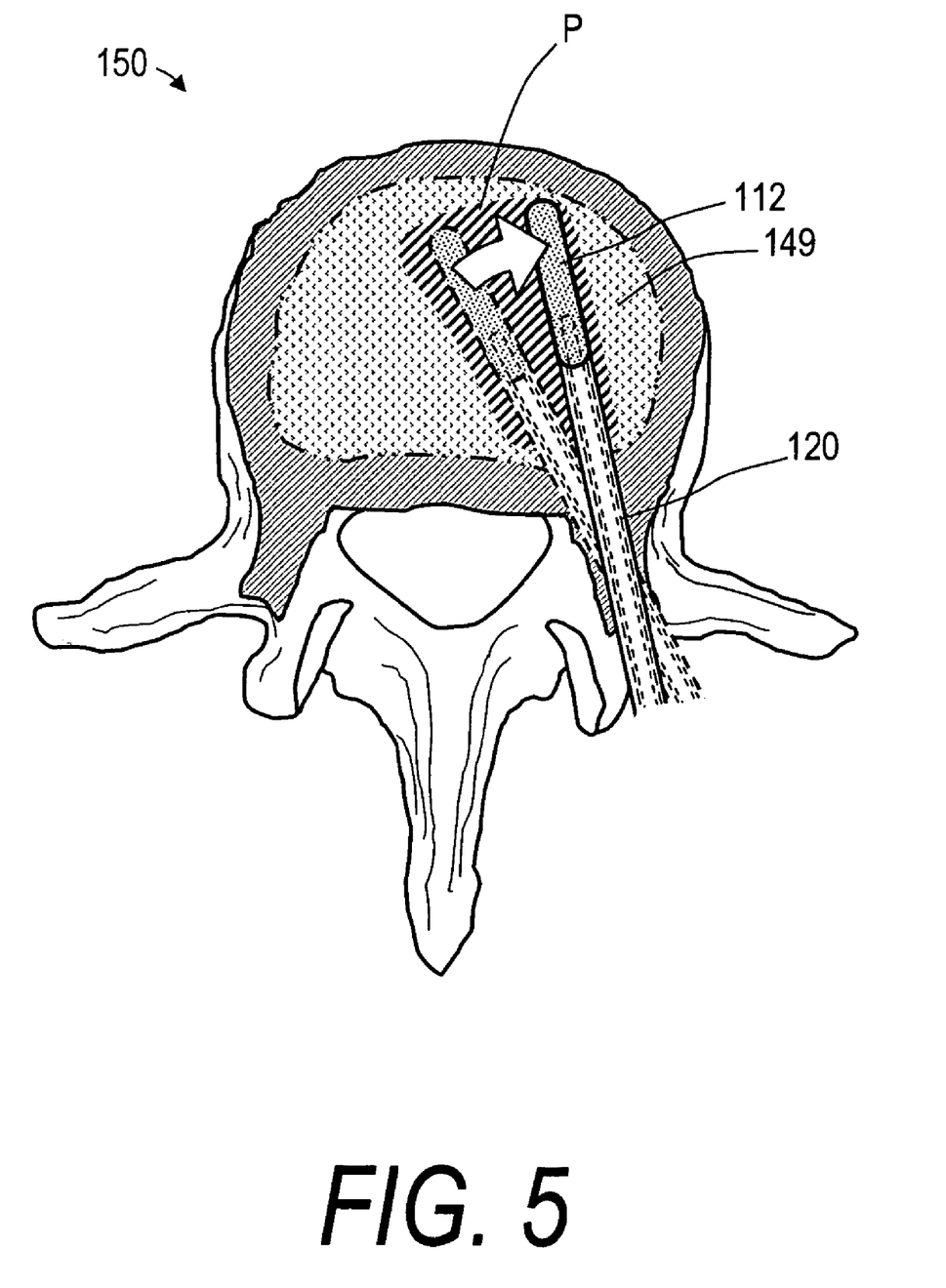
FIG. 5 is a sectional view of another vertebra showing a method of using the elastomeric cutter of FIG. 1 to abrade and cut a plane in cancellous bone of a vertebra.

FIG. 5 depicts another use of elastomeric cutter 112 in a vertebra wherein the working end 110 of the probe 100 is moved laterally and/or translated axially while rotating the elastomeric cutter 112 to abrade and cut a plane P. It can be understood that the cutting can be done from one or more access paths to the interior of the vertebra 150 to cut a suitable plane P. After cutting plane P, a bone fill material (e.g., PMMA) can be introduced in the plane P and increasing injection pressures of the bone fill material can be used to apply forces to move the endplates apart to reduce the fracture.

Figure 6:
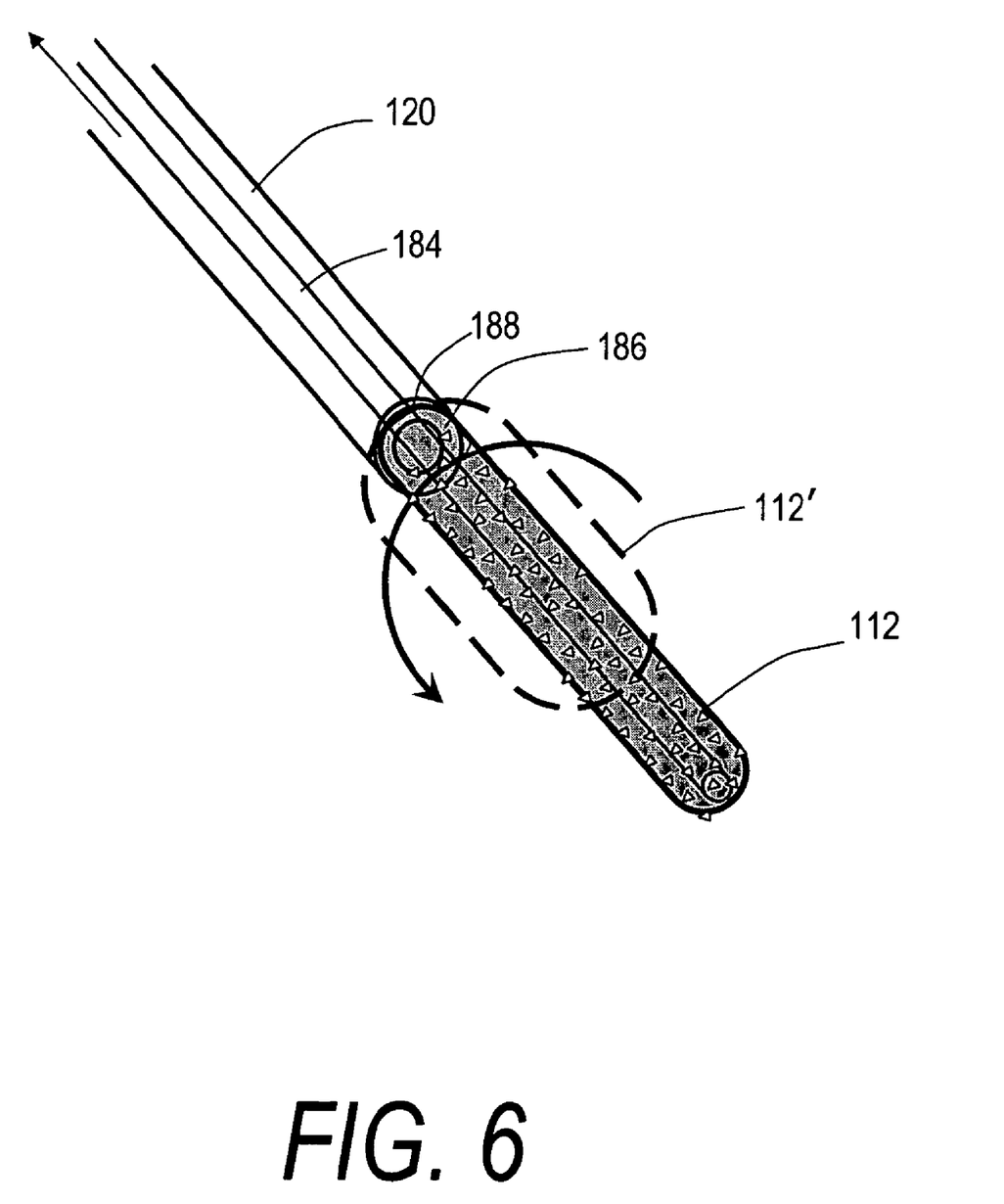
FIG. 6 is a perspective schematic view of the working end and elastomeric abrasive cutter of an alternative embodiment wherein the cutter is expandable in transverse section.

FIG. 6 depicts another probe 180 with an elastomeric cutter 112 similar to that of FIG. 1. In this embodiment, the motor-driven drive member 184 also functions as a pull-rod to axially compress and move the elastomeric cutter 112 to the shape indicated at 112' wherein the transverse section of the cutter is increased to thereby abrade or cut a larger diameter path in cancellous bone. In this embodiment, the cutter 112 can be an elastomeric monolith of silicone, urethane or the like that is bonded to drive member 184. It can be understood that the proximal end 186 of cutter 112 will be pushed against the distal end 188 of sleeve 120 to thereby outwardly expand the transverse section of the monolith. In the embodiment of FIG. 6, a central bore in the probe is not shown as in bore 128 in FIG. 1, but such a feature is optional.

Figure 7:
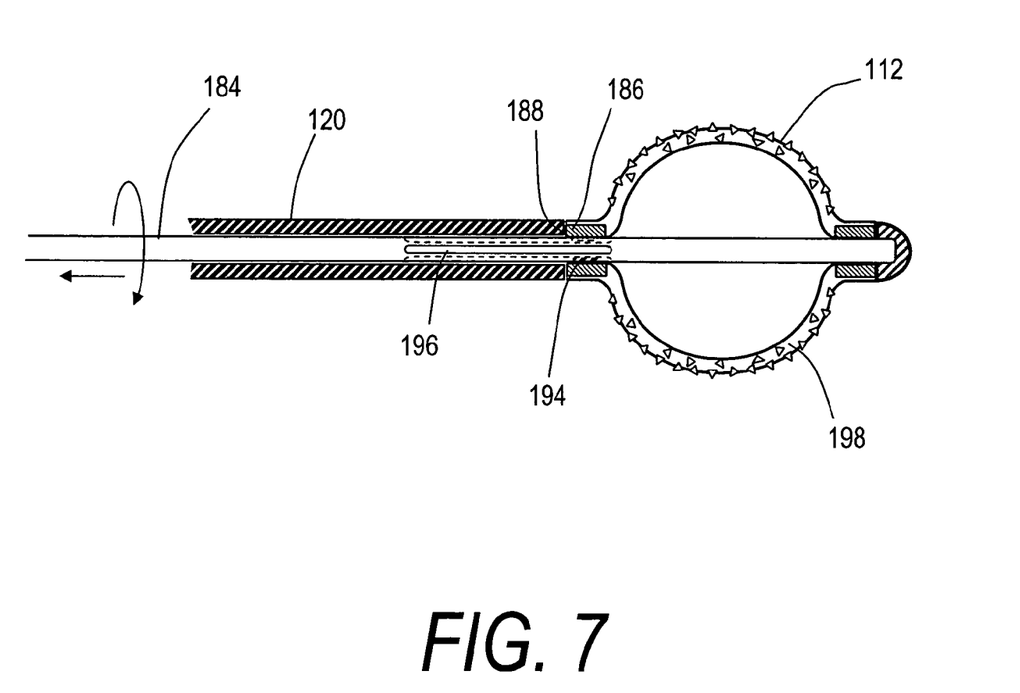
FIG. 7 is a sectional view of an alternative working end and elastomeric abrasive cutter that is expandable in transverse section.

FIG. 7 is a sectional view of another probe 190 with an elastomeric cutter 112 that is similar to that of FIG. 6. In the embodiment of FIG. 7, the motor-driven drive member 184 again functions as a pull-rod to actuate elastomeric cutter 112 to an enlarged transverse section. In this embodiment, the cutter 112 is hollow to allow greater expansion than the version of FIG. 6. It can be seen that elastomeric cutter 112 has first and second ends, 191a and 191b, that are bonded to first and second collars 192a and 192b that cooperate with drive shaft 184. The second collar is bonded to shaft 184 and the first collar included projecting key elements 194 that slide in key slots 196 to key the rotation of cutter 112 to that of the shaft 184. In all other respects, the system operates as described above. In another embodiment (not shown) the wall 198 of the elastomeric cutter 112 has a plurality of perforations and the interior opening communicates with aspiration ports in a hollow drive shaft and/or in the introducer sleeve. It can be easily understood that an aspiration source and irrigation source as in probe 100 of FIG. 1 can be incorporated into a system using a mechanically expandable elastomeric cutter 112 having a perforated wall.

Figure 8:
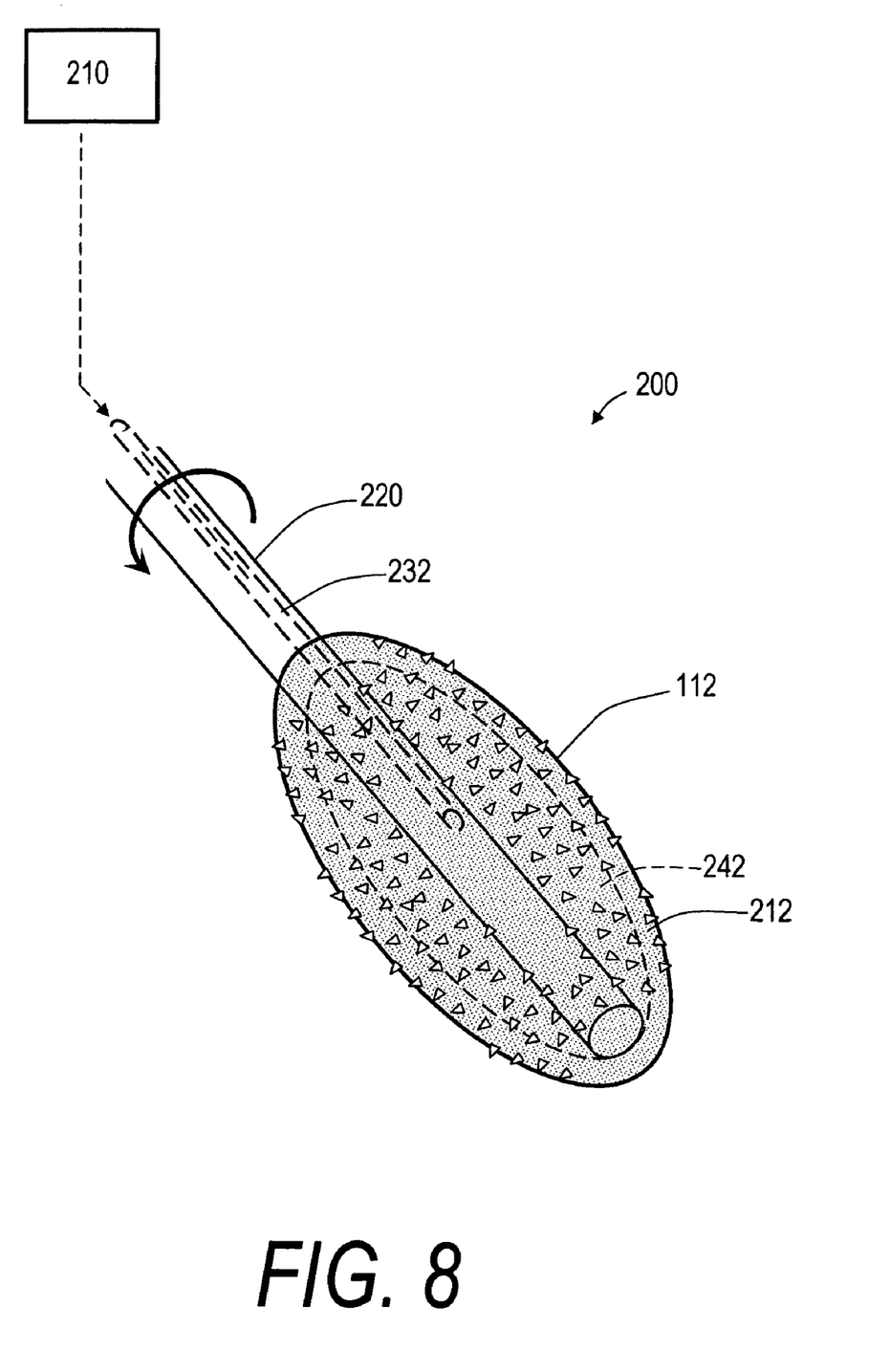
FIG. 8 is a sectional view of an alternative working end with a fluid-expanded elastomeric abrasive cutter that is expandable in transverse section.

FIG. 8 is a perspective sectional view of an alternative probe 200 that carries a rotatable elastomeric cutter 112 that is fluid expandable, for example, by inflow of a liquid or a gas from any suitable pressure source 210. The elastomeric cutter 112 has a substantially thick expandable wall 212 that carries diamond abrasives as described previously. The expandable wall is coupled to shaft 220 having a lumen 232 extending therethrough to deliver fluid from the pressurized source 210 to a chamber 242 in the expandable cutter 112. The shaft 220 can be a flexible polymer, a superelastic alloy or the like. As described previously, the probe can have a bore extending therethrough (not shown) for advancing over a straight or curved guide member. A plurality of differently shaped guide members can be used as shown in FIGS. 2B and 3 to create varied geometry paths.

In another embodiment similar to that of FIGS. 7 and 8, an expandable, elastomeric cutter 112 can be a resilient polymer without an inflation chamber that is expanded by centrifugal forces resulting from very high rotational speeds, for example 50,000 rpm or higher and can be driven by an air motor. In another embodiment, the wall of a similar balloon structure is expandable but can still be fluid-permeable to allow leakage of saline or sterile water into the bone being abraded. An aspiration source can be coupled to such a working end as described above.

FIGS. 9A-9D illustrate an alternative method wherein a fluid-expandable structure with an abrasive surface as in FIGS. 7 and 8 is used to create a space 240 (or multiple spaces) in cancellous bone 149 to receive a volume of bone cement. On aspect of the method includes abrading a space in a bone and injecting bone cement under high pressure to distract cortical endplates to restore vertebral height. In one embodiment, the bone cement is the type described in co-pending U.S. application Ser. Nos. 11/165,651 and 11/165,652 filed Jun. 24, 2005, both titled Bone Treatment Systems and Methods, wherein the bone cement can be altered in viscosity on demand with the application of energy to prevent cement extravasation.

The method of FIGS. 9A-9D provides safe means for creating a space 240 in a bone, for example a substantially large space in vertebral cancellous bone to receive a hone cement. In one prior art method known as kyphoplasty as described above the section titled "Description of The Related Art", a balloon is inserted in a cut or fractured path in cancellous bone 149 and then inflated with very high pressures. When inflating such a balloon, the bone structure acts akin to any ceramic material and only fractures under very large loads (e.g. up to 300 psi or more in the balloon)—at which time the fracture of cancellous bone is explosive. In kyphoplasty, the balloon is entirely constrained by the small path in cancellous bone until ever-increasing pressure fractures the cancellous bone resulting in "explosive" expansion of the balloon. The explosive expansion of a kyphoplasty balloon can cause point loading where the balloon contacts the cortical endplates of the vertebra. The explosive expansion of the balloon can easily crack an endplate if the expanded balloon wall is in close proximity to the endplate. When imaging the use of such a balloon device, it has been observed that the balloon moves explosively from a substantially collapsed condition to a fully expanded condition in an interval of less than a fraction of a second—the interval believed to be less than about one tenth of a second.

In contrast, the method of the invention depicted in FIGS. 9A-9D it is believed for the first time performs "non-explosive" balloon expansion with the interior of a vertebra by configuring the fluid-expandable structure with high speed rotational abrading functionality. At the same time, the inventive system removes bone debris by means of irrigation and aspiration to prevent the crushing and compaction of cancellous bone. The fluid-expandable structure 112 of FIGS. 9A-9C can be configured with an pressure source and controller so that the expandable structure is expanded with (i) constant pressure inflows, (ii) constant volume inflows, (iii) a modulated inflow rate or (iv) pulsed inflows to move the expandable structure 112 from a non-expanded condition to an expanded condition over an interval greater than about one tenth of a second. More specifically, the method includes moving the structure 112 from a non-expanded condition to an expanded condition over an interval ranging between about ¹⁄₁₀ of a second and 10 minutes, and more preferably between about 1 second and 5 minutes; and more preferably between about 10 seconds and 2 minutes.

Figure 9A:
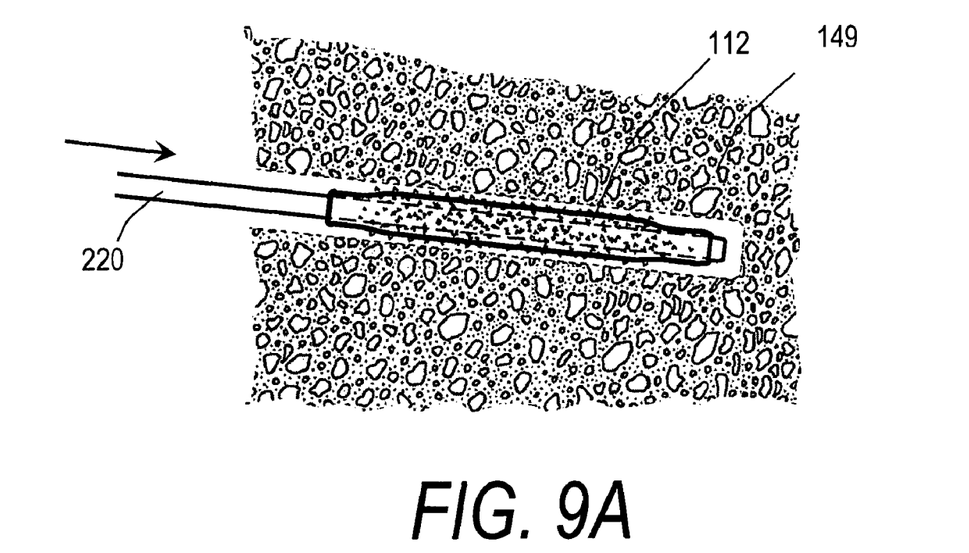
FIGS. 9A-9D are sequential views of a fluid-expandable elastomeric cutter being used to abrade a space in cancellous bone, for example, in a vertebra.
Figure 9B:
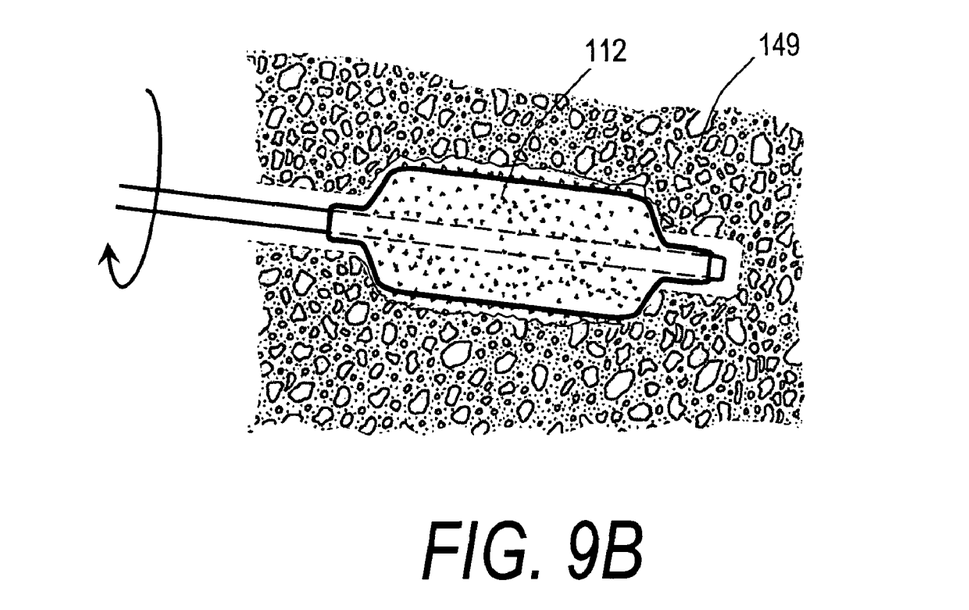
Figure 9C:
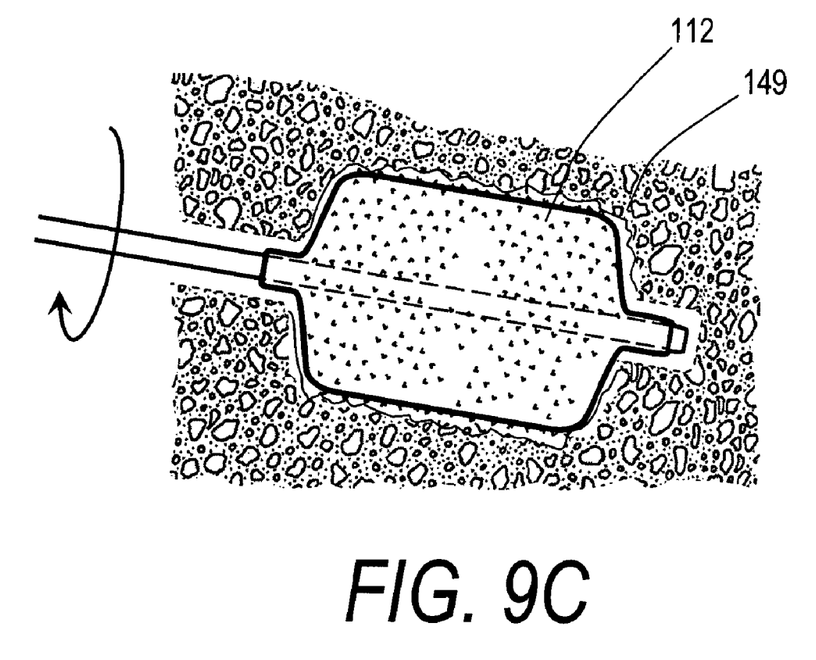
Figure 9D:
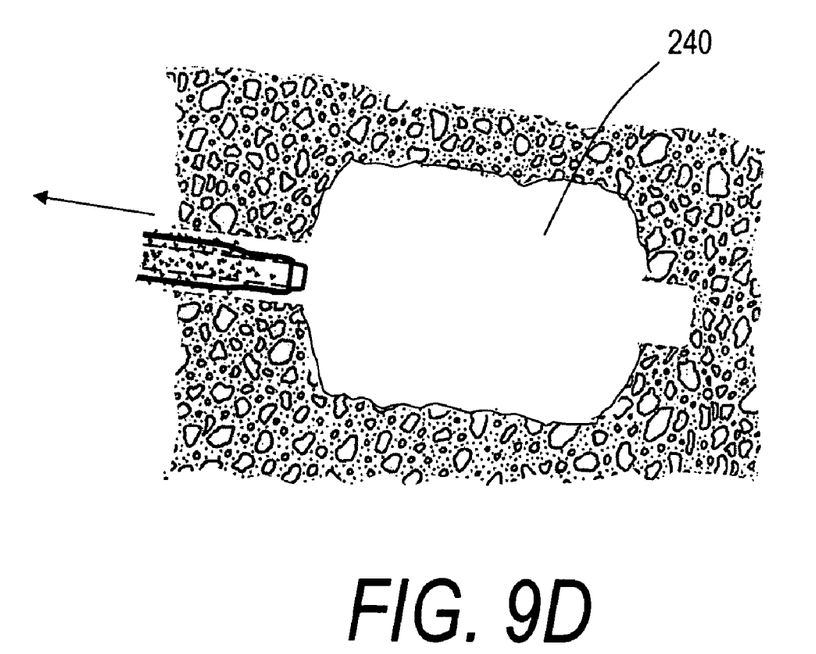

In another aspect of the method of FIGS. 9A-9C, the system uses a controller to expand the expandable structure 112 to a first increased transverse dimension (while rotationally abrading bone) and then expansion forces are terminated with the structure partially expanded—followed by at least one other interval to expand the structure to a second transverse dimension and then termination of expansion again while rotationally abrading bone. This method further insures that no explosive expansion forces are applied within a vertebral body as occurs with a kyphoplasty-type balloon and method. Stated another way, the method of the present invention allows for expansion of structure 112 in a plurality of intervals to increased dimensions that are a fraction of the most-expanded shape of the expandable structure 112 (FIGS.

9A-9C). For example, the expandable structure 112 can be expanded to 10%-50% of its maximum working volume after which inflows are terminated. Then the structure can be expanded to 20%-60% of its maximum working volume followed by a non-expansion interval, then the structure can be expanded to 30%-70% of its working volume followed by a non-expansion interval, and so forth. During the above steps of the method, the controller can rotate the structure 112 at a selected rpm or a varied rpm within the ranges described above.

In another aspect of the apparatus and method depicted in FIGS. 8 and 9A-9C, the system uses fluid expansion to move an expandable structure from a first transverse dimension to a second greater transverse dimension in cancellous bone of a vertebra at low non-explosive fluid inflow pressures while rotationally abrading the cancellous bone. The pressures can be less than 100 psi, or more preferably less than 50 psi, or more preferably less than 25 psi. The system pressures used by the inventive method are far lower than practiced in balloon procedures adapted to crush and compact cancellous bone.

In one aspect, a method of the invention comprises inserting an expandable structure into cancellous bone, and expanding the structure at a selected rate of expansion without compacting the cancellous bone by rotation of an abrasive surfaced structure to thereby cut bone. In another aspect of the invention, the method of the invention includes inserting an expandable structure into cancellous bone, and expanding the structure step-wise to insure that explosive expansion does not occur together with the rotational bone abrading step. In another aspect of the invention, the method includes inserting an expandable structure into cancellous bone, and expanding the structure with fluid inflow pulses that range from 1 Hz to 1,000 Hz to enhance bone abrasion with the surface of the expandable structure. More preferably, the fluid inflows are pulses in the range of 10 to 100 Hz.

In one aspect, the apparatus of the invention for abrading bone comprises (a) an elongated member having a first end and a second end, (b) the second end having an expandable cross-section with an abrasive surface, and (c) a rotational drive mechanism coupled to the first end for rotation thereof to abrade a path or a space in a bone. In an exemplary embodiment, the abrasive surface is a polymeric material with abrasive particles affixed thereto, such as diamond particles. The diamond particles can be natural monocrystalline diamond, synthetic monocrystalline diamond, polycrystalline diamond or a combination thereof. The diamond particles can a mean dimension ranging from about 1.0 micron to 100 microns.

In any of the above methods, the volume of bone cement volume can comprise a PMMA, monocalcium phosphate, tricalcium phosphate, calcium carbonate, calcium sulphate and hydroxyapatite, or any combination thereof. The bone cement also can carry allograft material, autograft material or any other infill bone infill granular material or scaffold material as in known in the art.

The above description of the invention intended to be illustrative and not exhaustive. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treating a vertebral body, comprising:
   introducing a distal end of an abrading device into an interior of a vertebral body, the distal end comprising an abrading structure attached to a pull rod, the abrading structure moveable between a first shape and a second shape, the abrading structure having a substantially continuous outer perimeter about the distal end of the abrading device;
   moving the pull rod proximally to compress the abrading structure against a distal end of an outer sleeve to thereby move the abrading structure from the first shape to the second shape, the outer sleeve positioned along the pull rod and proximally from the abrading structure; and
   rotating the abrading structure while moving the abrading structure toward the second shape thereby abrading bone.

2. The method of claim 1, wherein rotating the abrading structure is accomplished at from 500 to 400,000 rpm.

3. The method of claim 1, further comprising rotating the pull rod with respect to the outer sleeve.

4. The method of claim 1, wherein an inner surface of the abrading structure is bonded to an outer surface of the pull rod substantially along the inner surface of the abrading structure.

5. The method of claim 1, wherein moving the pull rod to compress the abrading structure forces a radial outward expansion of the abrading structure because an inner surface of the abrading structure is fixedly attached to the pull rod.

6. The method of claim 1, wherein the abrading structure comprises an elastomeric material.

7. The method of claim 6, wherein the elastomeric material comprises silicone or urethane.

* * * * *